US011109991B2

(12) United States Patent
Heiberg

(10) Patent No.: US 11,109,991 B2
(45) Date of Patent: Sep. 7, 2021

(54) ADJUSTABLE KNEE BRACE

(71) Applicant: Eric Heiberg, Long Valley, NJ (US)

(72) Inventor: Eric Heiberg, Long Valley, NJ (US)

( * ) Notice: Subject to any disclaimer, the term of this patent is extended or adjusted under 35 U.S.C. 154(b) by 479 days.

(21) Appl. No.: 15/943,869

(22) Filed: Apr. 3, 2018

(65) Prior Publication Data

US 2019/0298563 A1    Oct. 3, 2019

(51) Int. Cl.
*A61F 5/00* (2006.01)
*A61F 5/01* (2006.01)

(52) U.S. Cl.
CPC .... *A61F 5/0123* (2013.01); *A61F 2005/0134* (2013.01)

(58) Field of Classification Search
CPC ............ A61F 5/0123; A61F 2005/0134; A61F 2005/0132; A61F 5/013; A61F 5/0102; A61F 5/01; A61F 2005/0146; A61F 5/0125; A61F 2005/0167; A61F 2005/0137; A61F 2005/0151; A61F 5/0127; A61F 2005/0139
USPC ..................................................... 602/26, 16
See application file for complete search history.

(56) References Cited

U.S. PATENT DOCUMENTS

| | | | |
|---|---|---|---|
| 4,372,298 A | 2/1983 | Lerman | |
| 4,803,975 A | 2/1989 | Meyers | |
| 4,940,045 A | 7/1990 | Cromartie | |
| 5,302,169 A | 4/1994 | Taylor | |
| 5,554,105 A | 9/1996 | Taylor | |
| 5,586,970 A | 12/1996 | Morris et al. | |
| 5,766,140 A | 7/1998 | Tillinghast, III et al. | |
| 5,797,864 A | 8/1998 | Taylor | |
| 6,027,466 A * | 2/2000 | Diefenbacher | A61F 5/0125 602/16 |
| 6,387,066 B1 | 5/2002 | Whiteside | |
| 6,413,232 B1 | 7/2002 | Townsend et al. | |
| 6,527,733 B1 * | 3/2003 | Ceriani | A61F 5/0123 602/16 |
| 7,458,103 B2 | 12/2008 | Citterio et al. | |
| 2011/0112452 A1 | 5/2011 | Schiff | |
| 2018/0036159 A1 * | 2/2018 | Turrini | A61F 5/0102 |

FOREIGN PATENT DOCUMENTS

| | | |
|---|---|---|
| JP | 2017-522982 A | 8/2017 |
| KR | 10-2016-0020004 A | 2/2016 |
| WO | 01045600 A1 | 6/2001 |

* cited by examiner

*Primary Examiner* — Victoria J Hicks

(57) ABSTRACT

A knee brace with an articulation assembly connectable with a first cuff movable with respect to the articulation assembly about a first location defining a first pivot axis between the first cuff and articulation assembly, and movable about a second location defining a first rotation axis between the first cuff and articulation assembly. The knee brace may have a second cuff connectable with the articulation assembly and movable with respect to the articulation assembly about a third location defining a second pivot axis between the second cuff and articulation assembly. The second cuff is movable about a fourth location defining a second rotation axis between the second cuff and articulation assembly. The first pivot axis and first rotation axis may intersect each other or be offset from intersecting each other, the second pivot axis and second rotation axis may intersect each other or be offset from intersecting.

12 Claims, 9 Drawing Sheets

ADJUSTABLE KNEE BRACE

FIELD OF THE INVENTION

The present invention is directed to a knee brace having improved design, construction, functional and aesthetic features.

BACKGROUND OF THE INVENTION

A human knee joint is comprised of three compartments: 1) suprapatellar pouch and patellofemoral joint (includes the patella, patellofemoral joint, the trochlear notch of the femur, and synovial plicae); 2) medial (includes the medial femoral condyle, the medial tibia plateau, and the medial meniscus); and 3) lateral (includes the lateral femoral condyle, the lateral tibial plateau, and the lateral meniscus). Although a complicated joint, the various compartments and components of a healthy knee joint simply need to isolate the femur and tibia bones from contacting each other, and facilitate smooth movement between them. To this end, articular cartilage on the medial and lateral condyles of the femur, and on the tibial plateau, together with medial and lateral meniscus, serve to isolate the femur and tibia bones from each other.

A properly functioning knee joint relies heavily on the condition of the cartilage and meniscus. Degradation of these critical components results in functional degradation of the knee joint which, in turn, results in pain and discomfort, and possibly more limited mobility or immobility. Over time, the cartilage and/or meniscus may degrade and/or be damaged, resulting in a decrease in the isolative properties they are intended to provide. For example, osteoarthritis is a degenerative disease that can affect the knee joint, and that can result in wearing away of the articular cartilage over time. This typically occurs in the medial compartment sooner than in the other compartments, but multi- or tri-compartmental osteoarthritis is not uncommon. When the articular cartilage is damaged, degraded or no longer present on the femur, that can negatively affect the corresponding meniscus, and can ultimately lead to painful direct bone-on-bone contact between the femur and tibia.

There are non-surgical, therapeutic ways to address this pathology of the knee that typically involve modifying or adjusting the biomechanics of the knee joint. A knee brace can be used to effect this end. Knee braces intended to address symptoms of osteoarthritis shift the user's weight from the compartment with damaged cartilage to the compartment without damaged cartilage. Osteoarthritis knee braces accomplish this using a condyle pad to apply pressure laterally to the medial or lateral sides of the knee, and by using rigid or semi-rigid cuffs and straps that are generally fixed on the thigh and calf to pull or exert pressure on the thigh or calf in the direction opposite that of the condyle pad. These forces are sometimes called three-point loading and can modify or adjust the static and dynamic biomechanics of the knee joint. The intended effect of these forces is called unloading because the three-point loading unloads one of the knee compartments to dynamically change the condition of the knee joint and reduce the pain and discomfort associated with osteoarthritis. By changing the alignment of the femur, knee joint and tibia, such braces can compartmentally alter the amount of pressure experienced in the knee joint, e.g., by shifting the amount of pressure borne by one compartment to the other, for example from the medial compartment (typically bearing the most pressure), to the lateral compartment.

Some knee braces are intended to stabilize the knee joint or parts of the knee. For example, knee braces are provided that minimize lateral displacement of the knee joint in response to impact while allowing for near-normal use of the knee. This type of knee brace may be worn by football players, for example. Some knee braces are intended to immobilize or stabilize parts of the knee, such as the patella. For example, U.S. Pat. Nos. 5,554,105 and 5,797,864 (the entire contents for each of these patents being hereby incorporated herein by reference) are each directed to a knee brace that stabilizes the patella. These patents disclose structure intended to stabilize the patella with Y-shaped and U-shaped components that are held in place with a combination of rigid and non-rigid parts.

Knee braces intended to treat the symptoms of osteoarthritis may utilize a pad that is positioned near and in contact with the wearer's the knee—often referred to as a condyle pad because of its proximity to the medial and/or lateral condyle. This pad may be movable towards and away from the knee to vary the pressure applied to the knee joint in an effort to adjust and modify the static and dynamic condition of the knee. More specifically, the condyle pad is typically selectively moveable or adjustable towards and away from the knee to cause a change in the biomechanics of the knee joint. For example, it may be desirable to change the load-bearing characteristics of specific knee compartments, such as in a knee experiencing degradation of the medial compartment (without corresponding degradation of the lateral compartment) from osteoarthritis, where it may be desirable to relieve the load borne by the medial compartment. A knee brace with an adjustable medial condyle pad enables a wearer to change the load borne by the medial compartment, and hopefully provide relief to the pain and discomfort associated with osteoarthritis. However, knee braces provided in accordance with the teachings of the prior art require significant space between the knee brace and the knee to enable sufficient movement of the condyle pad. This results in knee braces that define, by their structural components, an envelope about the wearer's knee that is substantially larger than that defined by the wearer's knee.

In knee braces having a movable condyle pad there are at least three configurations. A first has a single point of movement for the condyle pad enabling movement of the pad towards and away from the knee joint. This enables the wearer to adjust the amount of pressure imparted by the condyle pad on the knee. In knee braces of this type, the condyle pad is caused to move along a line generally parallel with an axis defined by a rotation point of the knee brace, i.e., generally transverse to the knee. An exemplary patent teaching such a knee brace is U.S. Pat. No. 6,413,232 B1, the entire contents of which are hereby incorporated by reference. This patent teaches a knee brace with a condyle pad adjustable along an axis that is parallel and coaxial with a rotation axis of the knee brace. Movement of the condyle pad is also along a line that is perpendicular with a longitudinal axis of the knee brace. Thus, the angular relationship between the condyle pad and upper and lower cuffs is fixed.

A second configuration for knee braces with a movable condyle pad has at least two points of connection for the condyle pad, such as is disclosed in U.S. Pat. No. 7,485,103 B2, the entire contents of which are hereby incorporated herein by reference. Separate adjustment of the top and bottom of the condyle pad is not possible with this configuration, and the points of connection for the condyle pad may be generally parallel with but are not coaxial with the rotation axis of the knee brace. A variation of this configuration provides for two points of adjustment of the knee brace (see, e.g., U.S. Pat. Nos. 5,766,140 and 5,797,864, the entire contents of each of which is hereby incorporated herein by reference). These patents each teach two points of adjustment provided above and below, and outside an envelope defined by, the condyle pad, see, e.g., FIG. 4 of the '140 patent. The embodiments disclosed in this patent have two hinges 4, 4' located above and below the knee joint and flexion hinge 24 (located at the knee joint). Adjustment screws 49 are provided at each hinge for user adjustment of a condyle pad 26. This patent discloses embodiments comprising a single hinge 4, as well as two hinges 4, 4', each embodiment locating the hinge away from the flexion hinge 24. A third configuration for knee braces with a movable condyle pad has a pivot point of the condyle pad which provides for pivotable displacement of the condyle pad towards and away from the wearer's knee.

Exemplary prior art knee braces of this type can be found in U.S. Pat. Nos. 4,372,298, 4,940,045, and 5,586,970, the entire contents for each of these patents being hereby incorporated herein by reference. In each of these patents, adjustment of the condyle pad provides the wearer with the ability to adjust the knee brace before or after it is in place to attempt to alleviate the discomfort from osteoarthritis. Each of the devices disclosed in these patents is comprised of rigid and non-rigid components that typically perform the desired functions. For these patents, however, adjustment of the condyle pad is the feature that provides relief to the wearer. This is accomplished in a variety of ways. For example, U.S. Pat. No. 4,372,298 discloses a knee brace having a condyle pad on each side of the wearer's knee, each condyle pad being adjustable via a living hinge 70 (see, e.g., FIG. 6) that is located apart from a rotation axes defined by upper and lower pivot pins 44, 48. Another example is found in U.S. Pat. No. 4,940,045, that discloses a knee guard and brace with an adjustable medial condyle support pad. A condyle support pad 31 is secured to a plate 34 and connected to a rib 23 with a hinge 41 (see, e.g., FIG. 4) located above the knee joint and spaced away from the condyle pad (see, e.g., FIG. 1). Adjustment of the condyle pad is accomplished using a rotatable spacer 42 that includes a ramp 43. As can be seen in FIGS. 3 and 4, rotation of the spacer 42 causes displacement of the condyle support pad 31 towards and away from the wearer's knee. The pivot location of the hinge 41 and spacer 42 away from the knee joint, and away from rotatable connection of the upper and lower ribs 23, 24 at pin 26 results in the creation of a significant void between the ribs 23, 24 and condyle support pad 31, as shown in FIG. 1. This results in a knee brace having a larger profile at the knee joint, which may result in patients having to wear this brace outside of their clothing.

Yet another knee brace is disclosed in U.S. Pat. No. 5,586,970. The knee brace disclosed in this patent comprises a main structural hinge 41 that connects upper and lower struts 10, 14 at a hinge axis 42. The knee brace of this patent also has medial and lateral condyle pads 34, 36, each mounted to an upper strut 10 by a pivot pin 38 pivotable about horizontal pad axis 40. By providing a cam follower for each pivot pin 38, and by offsetting the pivot pin 38 with respect to hinge 41, the knee brace disclosed in this patent provides for dynamic adjustment of each condylar pad 34, 36, approximating "the dynamically changing center of pivot of the knee to hinge axis of main structural hinge 41." Column 5, lines 16-20. This is intended to provide a knee brace having a condyle pad that mimics the natural of movement of the knee joint, see, e.g., FIGS. 6-8. Each condyle pad is independently adjustable along horizontal pad axis 40, which is coaxial with pivot pin 38. See, e.g., FIGS. 2 and 3. The '970 patent teaches that it is preferred that pivot pins 38 (and pivot axis 40) are offset with respect to the axis 42 of the brace's main structural hinge 41 from ⅞" to 1⅜" (see, e.g., column 4, lines 51-54). This offset is provided to enable the knee brace to track "the relative movement of the supracondylar hollow of the femur with respect to the plateau of the fibula tibia." Column 3, lines 34-38. Thus, the '970 patent teaches a knee brace with a rotational axis 42 (corresponding to the brace's main structural hinge 41) that is offset from a pivot pin 38 coaxial with a pivot axis 40 and along which each condyle pad is adjustable.

In each of the above-identified patents, knee braces are disclosed having an axis of rotation located proximate with the natural flexion point of the knee. The knee braces also include a pivot axis or pivot point for a condyle pad that is offset from the axis of rotation. In some instances, such as with U.S. Pat. No. 5,586,970, separation of the pivot axis or pivot point from the axis of rotation is desired. Offsetting the pivot axis and rotation axis from each other typically results in a knee brace defining an envelope that is significantly larger than the wearer's knee (see, e.g., the '045 patent). Consequently, knee braces according to at least these prior art documents tend to take up a significant amount of space when worn, usually requiring that the brace be worn outside one's clothes.

Another prior art knee brace is disclosed in U.S. Pat. No. 5,302,169, the entire contents of which are incorporated herein. The '169 patent discloses a number of embodiments of a knee brace having rotation and pivot axes. It should be noted that what the '169 patent describes as a pivot point is described in the present application as a rotation axis. It should also be noted that what the '169 patent refers to as a hinge is described in the present invention as a pivot axis. Thus, the pivot points disclosed in the '169 patent are at least similar in function to the rotation axes of the present invention, and the hinge is at least similar in function to the pivot axis of the present invention. In this context, the '169 patent discloses a knee brace have two rotation axes disclosed as pivot points defined by bolts 40 (see, e.g., FIG. 2), and a pivot axis disclosed as a hinge 64. For each disclosed embodiment of the '169 patent, and using the terminology of the present invention, the rotation axes are spatially separated from each other, as are the pivot axes, and none of the foregoing intercept. In the embodiment of FIG. 4, a single pivot axis is disclosed as a hinge 64 between arms 18 and 22. In this embodiment, the rotation axes are spatially separated from each other, and a single pivot axis (defined by hinge 64) is offset from intersecting the rotation axes. In addition, the single pivot axis is located at a location that is equidistant from the rotation axes, locating the pivot axis at a center point between the rotation axes, and approximately a center point of the knee joint.

There thus exists a need for a knee brace that overcomes the foregoing and other shortcomings of the prior art.

SUMMARY OF THE INVENTION

Embodiments of the present invention provide a knee brace overcoming the above-described and other shortcomings of the prior art.

The present invention is directed to an improved knee brace that has many advantages over the prior art. In accordance with embodiments of the present invention, a knee brace comprises a first cuff connectable with an articulation assembly at a first location defining a first pivot axis, and at a second location defining a first rotation axis.

Preferably, the first rotation axis and first pivot axis intersect each other. An embodiment of the present invention further comprises a second cuff connectable with the articulation assembly at a third location defining a second pivot axis, and at a fourth location defining a second rotation axis, the second pivot axis and second rotation axis preferably intersecting each other. Alternatively, yet still preferably, the first rotation axis is offset from intersecting the first pivot axis, and the second rotation axis is offset from intersecting the second pivot axis, with neither the first pivot axis nor the second pivot axis being located at a location that is between and equidistant from the first and second rotation axes.

Alternatively, yet still preferably, a knee brace in accordance with embodiments of the present invention comprises a first cuff connected with an articulation assembly at a first location defining a first pivot axis, wherein an angle of inclination between the articulation assembly and the first cuff is adjustable, and wherein the brace defines an envelope about the joint when on the wearer's extremity, wherein the envelope does not increase with adjustment of the angle of inclination. This aspect of the present invention is possible, at least in part, because of the inventive positioning of the rotation and pivot axes—preferably intersecting or offset from intersecting and with neither the first nor second pivot axis at a location that is between and equidistant from the first and second rotation axes.

There are a number of advantages of locating the rotation and pivot axes to intersect, or to be offset from intersecting in accordance with embodiments of the present invention. An objective of certain types of knee braces is to relieve pain and discomfort of osteoarthritis. This is typically done by modifying the compartmental unloading of the knee joint to change its biomechanics. The present invention achieves this by locating both the pivot axis and rotation axis in relation to each other to provide a maximum effect on changing the biomechanics of the knee joint in a knee brace having a low profile when worn. A knee brace in accordance with embodiments of the present invention thus provides for adjustability of the knee brace at or near where the change in biomechanics should occur, i.e., at the knee joint. Advantageously, and preferably, the present invention accomplishes this with intersecting pivot and rotation axes. Alternatively, yet still preferably, the present invention also accomplishes this by non-intersecting pivot and rotation axes that are still relationally located to provide maximum benefits to the wearer, and minimum profile for a knee brace.

Moreover, a knee brace in accordance with embodiments of the present invention provides both a pivot axis and a rotation axis that either intersect each other, or that are offset from intersecting yet not located at a location between and equidistant from the rotation axes, thereby providing adjustment means aligned with the natural anatomy of the leg and knee. The inventive knee brace thus conforms closely to the natural anatomy of the knee. In contrast, prior art knee braces provide for adjustment means away from the center of the knee and fail to align with the natural anatomy of the leg.

A further advantage of a knee brace in accordance with embodiments of the present invention is a low-profile brace that minimally increases a brace envelope defined by the brace when it is in place on the wearer's extremity. Prior art knee braces have significant variation in the brace envelope because the size of the brace envelope changes significantly as the brace is adjusted. This is due, at least in part, to the amount of space required with such braces to adjust the loading and unloading of the knee joint. As noted, prior art knee braces separate the rotation and pivot axes, locating the pivot axis (axes) away from the joint, resulting in a significant increase in the brace envelope when the brace is adjusted. Consequently, prior art knee braces are bulky, and typically must be worn outside the wearer's clothes.

In accordance with embodiments of the present invention, at least one of an upper cuff and a lower cuff is connected with an articulation assembly at rotation and pivot axes, with each pair (i.e., one pair for the upper cuff, one pair for the lower cuff) of pivot and rotation axes being located in close proximity to each other, preferably intersecting. For example, the pivot axis for the upper cuff is in close proximity to, or intersects, the rotation axis for the upper cuff. This enables adjustable, pivotable articulation of the knee brace at or near the rotation axis, controlling pressure imparted to the knee from a condyle pad located in contacting proximity to the knee. This ensures that the condyle pad maintains contact with the knee, and that the upper and lower cuffs are always in intimate contact with parts of the wearer's thigh and calf. As a result, embodiments of the present invention provide a low-profile knee brace. In a low-profile brace, the width of the knee and brace together (as viewed from the front), and the envelop of the joint area are minimized. Patients desire a low-profile brace because it can be worn beneath clothing, does not hinder them while walking (it does not bump into objects when walking), and has a streamlined appearance. In addition, research shows that a low-profile osteoarthritis brace increases patient compliance.

Research also shows that an easily patient adjustable osteoarthritis brace increases patient comfort level. Different amounts of unloading provide different amounts of pain relief. Different amounts of brace adjustment provide different amounts of unloading. Different patients require different amounts of pain relief/adjustment of the brace. Even the same patient requires different amounts of pain relief/adjustment throughout the day. An easily adjustable brace will encourage the patient to adjust the brace and will therefore increase patient pain relief and comfort.

Other braces require tools to perform an adjustment—tools that may be lost or that are not always readily available. When tools are not readily available, the patient is discouraged from making an adjustment and his/her pain level is not reduced.

A knee brace in accordance with embodiments of the present invention employs a mechanical advantage that enables the user to adjust the brace at any location at any time without the need for special tools or training. The mechanical advantage is provided by various parts of the inventive knee brace and make it easy to adjust the knee brace without significant effort, and without the need for tools or other assistance. If the mechanical advantage is not sufficient (such as for elderly patients who may require a high degree of unloading of a joint), embodiments of the present invention include additional features and structure to further enhance the mechanical advantage, such as, by way of non-limiting example, slots to accept a coin or other similarly sized and shaped disk-like object. Common currency coins are readily available almost everywhere there are people; using a coin, the user can employ an increased mechanical advantage and adjust the brace at any location at any time. Thus, the present invention encourages the patient to adjust the brace and will therefore increase his/her pain relief and comfort.

A brace that is adjusted to provide too much unloading applies excessive forces to the leg, which can cause pain and discomfort. Typically, a patient may balance the pain relief from unloading against pain caused by an excessive adjustment. Other braces are adjustable only in discrete, preset increments. This is a hindrance to a user whose pain management requires a setting between two available discreet increments. In accordance with embodiments of the present invention, a knee brace is provided that is adjustable between the minimum and maximum levels of unloading, as desired by the user or wearer, without preset, discrete, fixed settings. In addition, adjustment of the knee brace of the present invention is not limited to discrete, preset increments. Rather, the knee brace of the present invention is adjustable over an infinite number of settings between end points of the adjustment range. Thus, a wearer can adjust the knee brace of the present invention for optimal comfort, pain relief and unloading.

Embodiments of the present invention also include a visual indicator of the adjustment setting for the user's quick reference and guidance Although the disclosure provided herein is directed primarily to a knee brace for a human knee, it will be obvious to a person skilled in the art from such disclosure that the present invention is not limited to such an application. Rather, a knee brace in accordance with embodiments of the present invention is usable on any joint of any animal.

An embodiment of the present invention is directed to a brace wearable on an extremity of a wearer, the extremity having a joint, and the brace comprising a first cuff placeable on the extremity, an articulation assembly connected with the first cuff such that the first cuff is movable with respect to the articulation assembly about a first location defining a first pivot axis between the first cuff and articulation assembly, and the first cuff is movable with respect to the articulation assembly about a second location defining a first rotation axis between the first cuff and articulation assembly, wherein the first pivot axis and the first rotation axis intersect each other.

An embodiment of the present invention is further directed to a brace wearable on an extremity of a wearer, wherein the articulation assembly further comprises, a base, a mount connected to the base at the first location, and connected to the first cuff at the second location, and an adjuster manipulable to cause the first cuff to pivot about the first pivot axis.

An embodiment of the present invention is further directed to a brace wearable on an extremity of a wearer, wherein the adjuster comprises, a wedge movable along a surface of the mount to cause the first cuff to pivot about the first pivot axis, a stud engaged with a part of the wedge such that manipulation of the stud causes movement of the wedge along the surface of the mount, and a head manipulable to cause manipulation of the stud.

An embodiment of the present invention is further directed to a brace wearable on an extremity of a wearer, wherein the first cuff further comprises a second part defining a first plane, and wherein the base defines a second plane, and wherein the first rotation axis intersects the first plane at a fixed angle, and the second plane at a variable angle.

An embodiment of the present invention is further directed to a brace wearable on an extremity of a wearer, wherein the variable angle is variable by the adjuster.

An embodiment of the present invention is further directed to a brace wearable on an extremity of a wearer, wherein the mount further comprises a boss, and wherein the articulation assembly further comprises a rotation pin connectable with the boss to connect the mount and the first cuff together at the second location.

An embodiment of the present invention is further directed to a brace wearable on an extremity of a wearer, wherein the mount further comprises a tab, and wherein the articulation assembly further comprises a pivot pin connectable with the tab to connect the mount and the first cuff together at the first location.

An embodiment of the present invention is further directed to a brace wearable on an extremity of a wearer, wherein the first cuff is movable with respect to the articulation assembly in a first pivot direction about the first location defining the first pivot axis between the first cuff and articulation assembly, and wherein the first cuff is movable with respect to the articulation assembly in a first rotation direction about the second location defining the first rotation axis between the first cuff and articulation assembly.

An embodiment of the present invention is further directed to a brace wearable on an extremity of a wearer, wherein the brace further comprises a second cuff placeable on the extremity, the articulation assembly being connected with the second cuff such that the second cuff is movable with respect to the articulation assembly about a third location defining a second pivot axis between the second cuff and articulation assembly, and the second cuff is movable with respect to the articulation assembly about a fourth location defining a second rotation axis between the second cuff and articulation assembly, wherein the second pivot axis and the second rotation axis intersect each other.

An embodiment of the present invention is further directed to a brace wearable on an extremity of a wearer, wherein the second cuff is movable with respect to the articulation assembly in a second pivot direction about the third location defining the second pivot axis between the second cuff and articulation assembly, and wherein the second cuff is movable with respect to the articulation assembly in a second rotation direction about the fourth location defining the second rotation axis between the second cuff and articulation assembly.

An embodiment of the present invention is further directed to a brace wearable on an extremity of a wearer, wherein the first cuff is rotatable about the first rotation axis, and the second cuff is rotatable about the second rotation axis, wherein the knee brace further comprises a gear having a first part defined on the first cuff, and a second part defined on the second cuff, wherein the first part and the second part engage each other such that movement of one of the first cuff and second cuff causes movement of the other one of the first cuff and second cuff.

An embodiment of the present invention is further directed to a brace wearable on an extremity of a wearer, wherein the gear further comprises first teeth on the first cuff, and second teeth on the second cuff, wherein the first teeth and the second teeth movably interlockingly engage such that rotational movement of one of the first cuff and second cuff causes corresponding rotational movement of the other one of the first cuff and second cuff.

An embodiment of the present invention is further directed to a brace wearable on an extremity of a wearer, wherein a surface on at least one of the teeth of the first and second teeth is contoured.

An embodiment of the present invention is further directed to a brace wearable on an extremity of a wearer, wherein the articulation assembly further comprises a base, a first mount connected to the base at the first location, and connected to the first cuff at the second location, a second mount connected to the base at the third location, and connected to the second cuff at the fourth location, and an adjuster manipulable to cause the first cuff to pivot about the first pivot axis and the second cuff to pivot about the second pivot axis.

An embodiment of the present invention is further directed to a brace wearable on an extremity of a wearer, wherein the adjuster further comprises one of a head manipulable to cause the first cuff to pivot about the first pivot axis and the second cuff to pivot about the second pivot axis, or a first head and a second head, the first head being manipulable to cause the first cuff to pivot about the first pivot axis, and the second head manipulable to cause the second cuff to pivot about the second pivot axis.

Another embodiment of the present invention is directed to a brace wearable on an extremity of a wearer, the extremity having a joint, the brace comprising a first cuff placeable on the extremity, and an articulation assembly connected with the first cuff at a first location defining a first pivot axis, wherein an angle of inclination between the articulation assembly and the first cuff is adjustable, and wherein the brace defines an envelope about the joint when on the wearer's extremity, wherein the envelope does not increase with adjustment of the angle of inclination.

An embodiment of the present invention is further directed to a brace wearable on an extremity of a wearer, wherein the brace further comprises a second cuff placeable on the extremity, the articulation assembly being connected with the second cuff at a third location defining a second pivot axis, and at a fourth location defining a second rotation axis.

Another embodiment of the present invention is directed to a brace wearable on an extremity of a wearer, the extremity having a joint, the brace comprising a first cuff placeable on a first part of the extremity, a second cuff placeable on a second part of the extremity, and an articulation assembly connected with the first cuff and the second cuff. The first cuff is movable with respect to the articulation assembly about a first location defining a first pivot axis between the first cuff and articulation assembly, and the first cuff is movable with respect to the articulation assembly about a second location defining a first rotation axis between the first cuff and articulation assembly. The second cuff is movable with respect to the articulation assembly about a third location defining a second pivot axis between the second cuff and articulation assembly, and the second cuff is movable with respect to the articulation assembly about a fourth location defining a second rotation axis between the second cuff and articulation assembly, wherein the first pivot axis and the first rotation axis are offset from intersecting each other, and wherein the second pivot axis and the second rotation axis are offset from intersecting each other, neither of the first pivot axis nor the second pivot axis being located at a location that is between and equidistant from the first and second rotation axes.

An embodiment of the present invention is further directed to a brace wearable on an extremity of a wearer, wherein the first cuff is movable with respect to the articulation assembly in a first pivot direction about the first location defining the first pivot axis between the first cuff and articulation assembly, and wherein the first cuff is movable with respect to the articulation assembly in a first rotation direction about the second location defining the first rotation axis between the first cuff and articulation assembly. Wherein the second cuff is movable with respect to the articulation assembly in the second pivot direction about the third location defining the second pivot axis between the second cuff and articulation assembly, and wherein the second cuff is movable with respect to the articulation assembly in a second rotation direction about the fourth location defining the second rotation axis between the second cuff and articulation assembly.

An embodiment of the present invention is further directed to a brace wearable on an extremity of a wearer, wherein the articulation assembly further comprises a base, a first mount connected to the base at the first location, and connected to the first cuff at the second location, a second mount connected to the base at the third location, and connected to the second cuff at the fourth location, and an adjuster manipulable to cause at least one of the first cuff or the second cuff to pivot about the first pivot axis or the second pivot axes, respectively.

An embodiment of the present invention is further directed to a brace wearable on an extremity of a wearer, wherein the adjuster comprises a wedge movable along a surface of one of the first and second mount to cause one of the first cuff or second cuff to pivot about the first pivot axis or second pivot axis, respectively, a stud engaged with a part of the wedge such that manipulation of the stud causes movement of the wedge along the surface of the one of the first or second mount, and a head manipulable to cause manipulation of the stud.

An embodiment of the present invention is further directed to a brace wearable on an extremity of a wearer, wherein the articulation assembly further comprises a base, and wherein the first cuff further comprises a second part defining a first plane, and wherein the second cuff further comprises a second part defining a second plane, wherein the base defines a third plane, and wherein the first rotation axis intersects the first plane at a fixed angle, and intersects the third plane at a variable angle, and wherein the second rotation axis intersects the second plane at a fixed angle, and intersects the third plane at a variable angle.

An embodiment of the present invention is further directed to a brace wearable on an extremity of a wearer, wherein the articulation assembly further comprises an adjuster, and wherein the variable angle is variable by the adjuster.

An embodiment of the present invention is further directed to a brace wearable on an extremity of a wearer, wherein the first and second mount each further respectively comprise a first boss and a second boss, and wherein the articulation assembly further comprises a first rotation pin connectable with first boss to connect the first mount and the first cuff together at the second location, and a second rotation pin connectable with the second boss to connect the second mount and the second cuff together at the fourth location.

An embodiment of the present invention is further directed to a brace wearable on an extremity of a wearer, wherein the first and second mount each further respectively comprise a first tab and a second tab, and wherein the articulation assembly further comprises a first pivot pin connectable with the first tab to connect the first mount and the first cuff together at the first location, and a second pivot pin connectable with the second tab to connect the second mount and the second cuff together at the third location.

Another embodiment of the present invention is directed to a brace wearable on an extremity of a wearer, brace wearable on an extremity of a wearer, the extremity having a joint, the brace comprising a first cuff placeable on the extremity, and an articulation assembly connected with the first cuff, wherein the first cuff is movable with respect to the articulation assembly about a first location defining a first pivot axis between the first cuff and articulation assembly, and wherein the first cuff is movable with respect to the articulation assembly about a second location defining a first rotation axis between the first cuff and articulation assembly, wherein the first pivot axis and the first rotation axis are offset from intersecting each other. The articulation assembly further comprises a base, a mount connected to the base at the first location, and connected to the first cuff at the second location, and an adjuster manipulable to cause the first cuff to pivot about the first pivot axis.

An embodiment of the present invention is further directed to a brace wearable on an extremity of a wearer, wherein the first cuff is movable with respect to the articulation assembly in a first pivot direction about the first location defining the first pivot axis between the first cuff and articulation assembly, and wherein the first cuff is movable with respect to the articulation assembly in a first rotation direction about the second location defining the first rotation axis between the first cuff and articulation assembly.

An embodiment of the present invention is further directed to a brace wearable on an extremity of a wearer, wherein the first pivot axis is located at a location between the rotation axis and the joint.

DESCRIPTION OF THE DRAWINGS

Embodiments of the present invention will now be described with reference to the following figures, wherein.

DESCRIPTION OF EMBODIMENTS OF THE INVENTION

The following describes exemplary embodiments of the present invention. It should be apparent to those skilled in the art from the disclosure provided herein that the described embodiments of the present invention are illustrative and not limiting, having been presented by way of example only. All features disclosed in this description may be replaced by alternative features serving the same or similar purpose, unless expressly stated otherwise. Therefore, numerous and various other embodiments are contemplated as falling within the scope and spirit of the present invention. In addition, embodiments of the present invention comprising similar features and structure may be described singularly (e.g., description of an upper cuff without a corresponding description of a similar lower cuff). It will be obvious to persons skilled in the art, and from the disclosure provided herein, that such discussion and description of a first feature or structure is intended to, and does cover a second similar feature or structure, unless expressly disclosed to the contrary.

Figure 1:
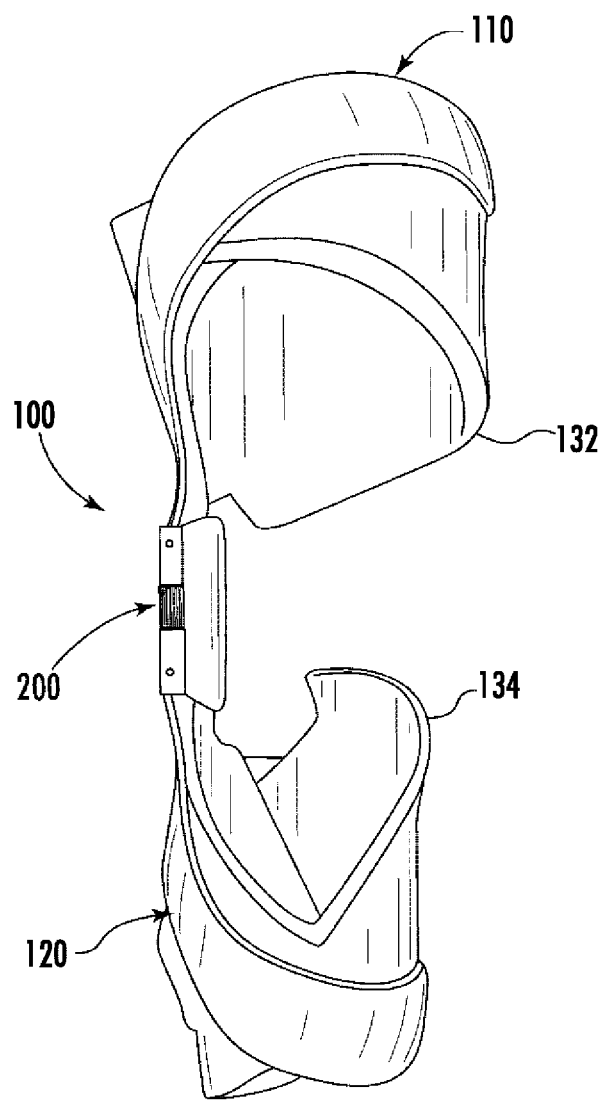
FIG. 1 depicts a front view of a knee brace for a right leg in accordance with an embodiment of the present invention.
Figure 2:
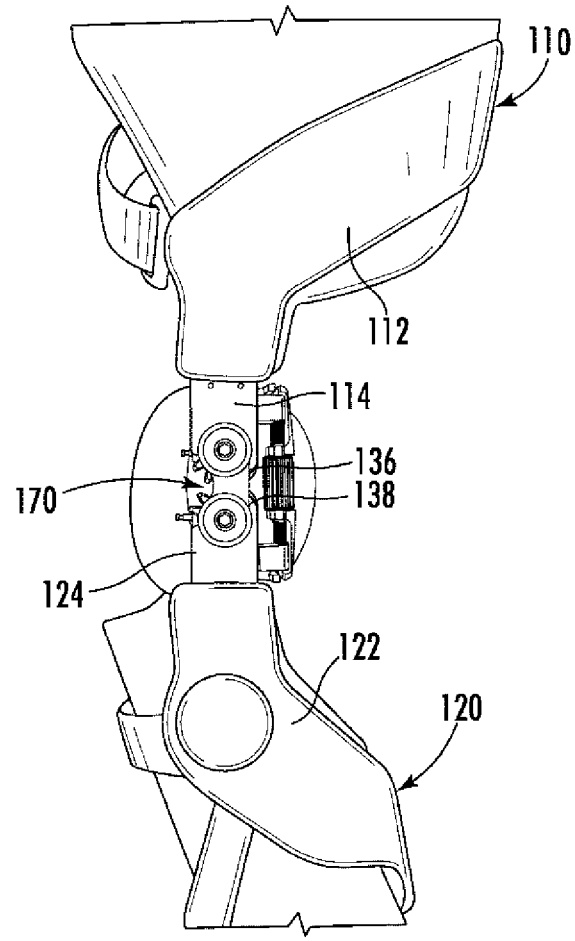
FIG. 2 depicts a right-side view of the knee brace of FIG. 1.
Figure 3:
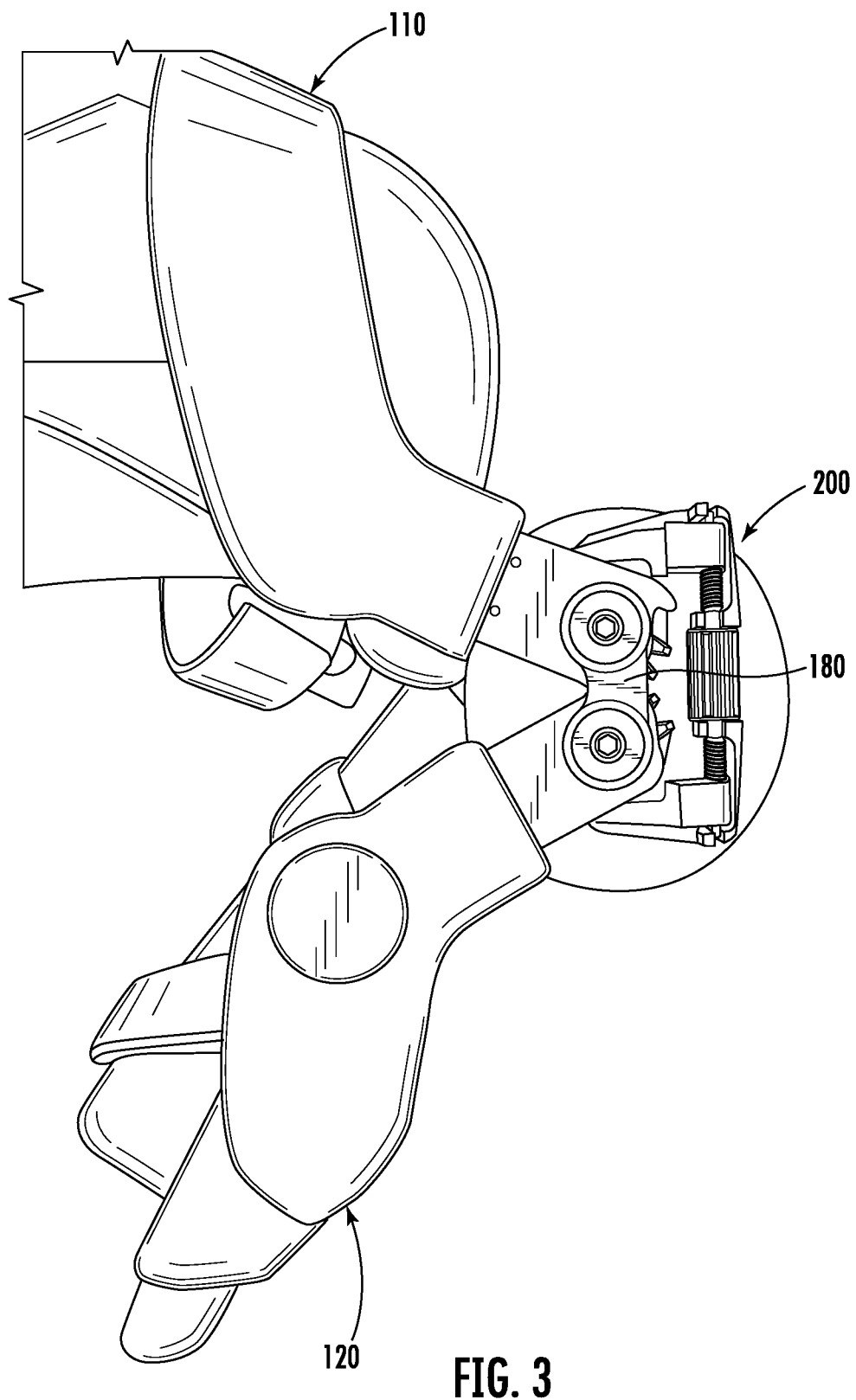
FIG. 3 depicts a right-side view of the knee brace of FIG. 1 in a flexed position.

A knee brace 100 in accordance with embodiments of the present invention is depicted in FIGS. 1, 2 and 3. The knee brace 100 depicted in the figures and described herein is intended to be worn on the right leg of a human and to unload the medial compartment of the knee. It will be obvious to a person of skill in the art that the disclosure of the present invention applies equally for a brace to be worn on the right leg of a human to unload the lateral compartment of the knee, as well as to be worn on the left leg of a human, as well as a brace to be worn near a joint of any animal. The knee brace 100 comprises an upper cuff 110, a lower cuff 120, and an articulation assembly 200. The upper cuff 110 is designed and configured to fit around a part of a wearer's thigh, and the lower cuff 120 is designed and configured to fit around a part of the wearer's calf. An upper sleeve 132 fits within and is secured to the upper cuff 110, and a lower sleeve 134 fits within and is secured to the lower cuff 120, each providing a comfortable fitting between the cuff 110, 120 and the part of the wearer's thigh and calf, respectively. Each of the upper and lower cuffs 110, 120 and/or sleeves 132, 134 may have one or more straps, connectors, fasteners, etc. (not shown) usable to adjust the fit of the cuff 110, 120 and/or sleeve 132, 134 around the part of the wearer's thigh and calf, respectively.

Figure 4A:
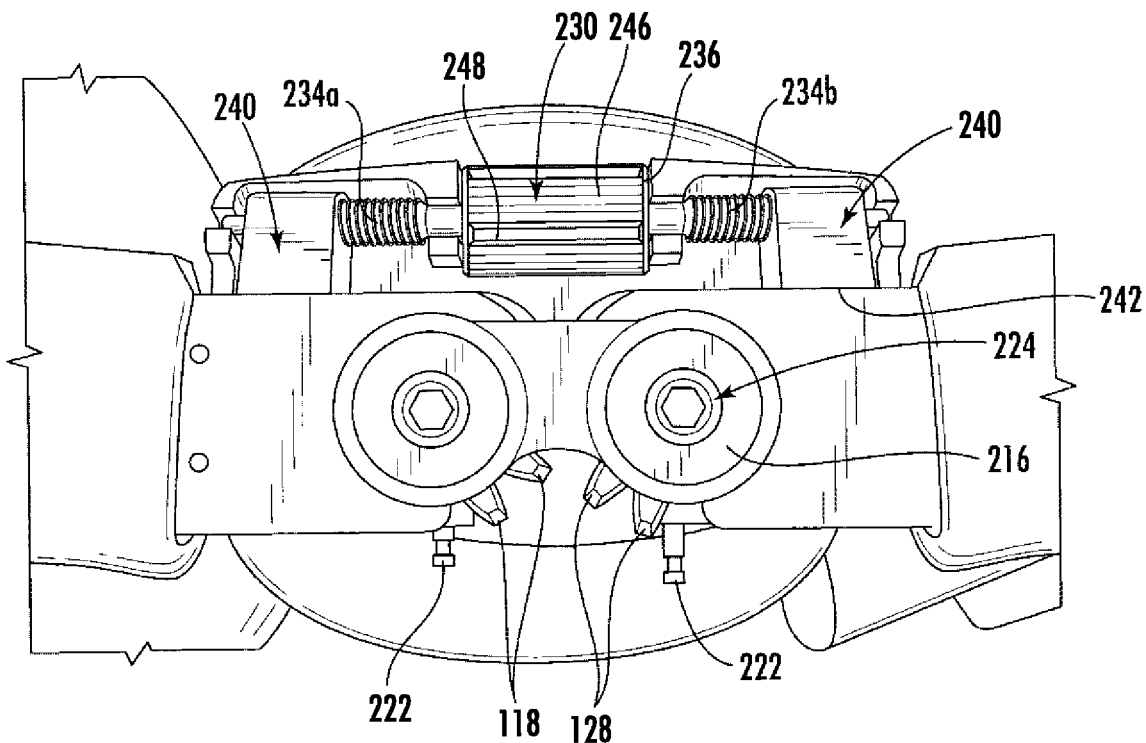
FIG. 4A depicts a view of an articulation assembly of a knee brace with both upper and lower cuffs in accordance with an embodiment of the present invention.
Figure 4B:
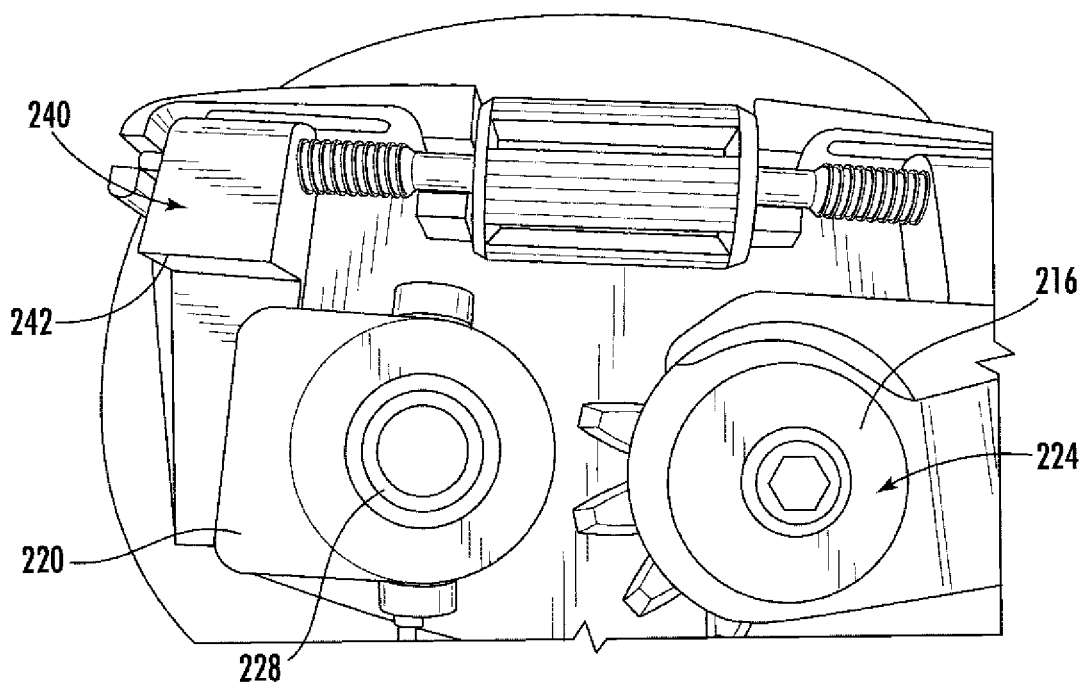
FIG. 4B depicts a view of an articulation assembly of a knee brace with the upper cuff removed.

The upper cuff 110 has a first part 112 that has a generally contoured shape complementary with the shape of a human thigh. The first part 112 may be made from metal, carbon fiber, fiberglass, or other similar material, as a routine matter of design choice, and may be covered with a material providing protective and/or aesthetic properties and characteristics. The upper cuff 110 further comprises a second part 114 connected to or unitarily formed with the first part 112. The second part 114 extends from the first part 112 away from the wearer's thigh and towards the wearer's knee. The second part 114 has a free end 136 with a plurality of teeth 118 (see, e.g., FIG. 4A). It will be obvious to a person skilled in the art and based upon the disclosure provided herein that structure alternative to the disclosed teeth 118 may be defined or provided at free end 136, provided that such alternative structure performs the function(s) of the teeth 118 described herein.

Figure 12:
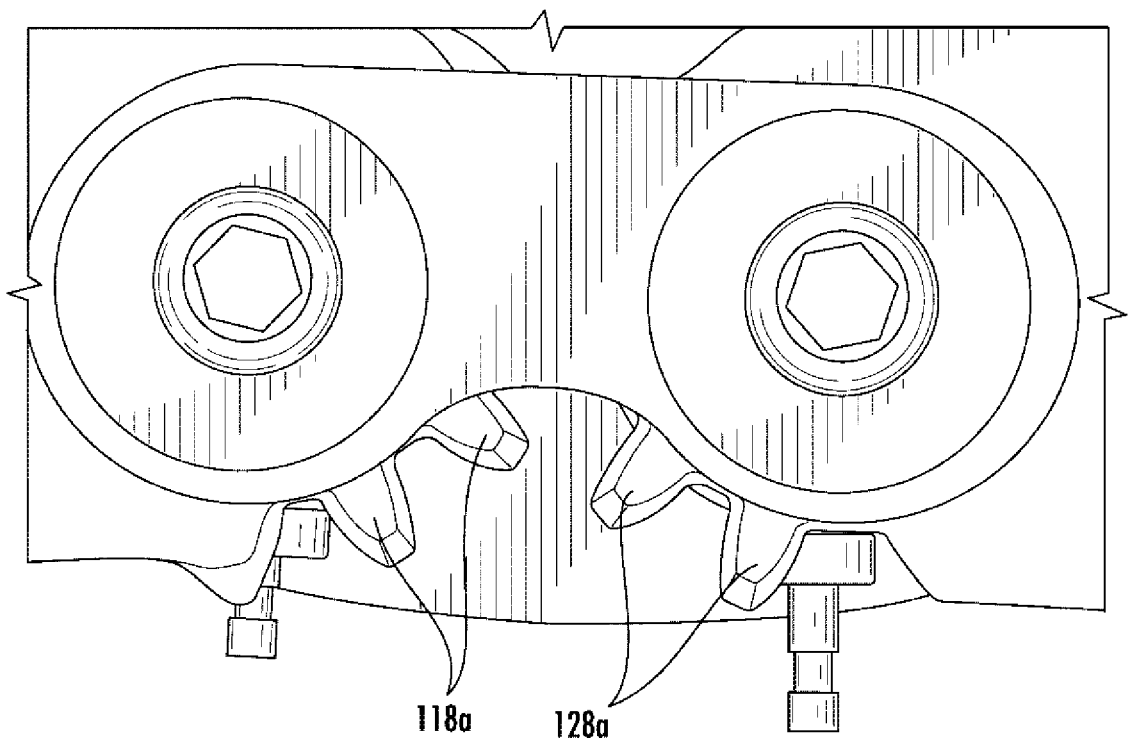
FIG. 12 depicts a detail view of the teeth of a gear in accordance with embodiments of the present invention.

The lower cuff 120 has a first part 122 that has a generally contoured shape complementary with the shape of a human calf. The first part 122 may be made from metal, carbon fiber, fiberglass, or other similar material, as a routine matter of design choice, and may be covered with a material providing protective and/or aesthetic properties and characteristics. The lower cuff 120 further comprises a second part 124 connected to or unitarily formed with the first part 122. The second part 124 extends from the first part 122 away from the wearer's calf and towards the wearer's knee. The second part 124 has a free end 138 with a plurality of teeth 128 (see, e.g., FIG. 4A). It will be obvious to a person skilled in the art and based upon the disclosure provided herein that structure alternative to the disclosed teeth 128 may be defined or provided in the free end 138, provided that such alternative structure performs the function(s) of the teeth 128 described herein. The teeth 118 of upper cuff 110 engage the teeth 128 of lower cuff 120 to form a gear 170 so that movement of one of the upper cuff 110 and lower cuff 120 causes movement of the other one, as shown in FIG. 3. It will be obvious to a person skilled in the art, and from the disclosure provided herein, that other structures are contemplated by, and with the scope and spirit of the present invention for providing the functionality of the gear 170. The aforementioned description providing but one embodiment. As noted, a knee brace 100 in accordance with embodiments of the present invention may comprise an upper cuff 110 and a lower cuff 120 rotatingly engaged by a gear 170 comprised of teeth 118 on a free end 136 of the upper cuff 110, and teeth 128 on a free end 138 of the lower cuff 120. In addition to each of the upper cuff 110 and lower cuff 120 being rotatable about separate rotation axes, they are each pivotable about separate pivot axes. They can thus simultaneously rotate and pivot about their respective axes. To ensure smooth rotation of each of the upper and lower cuff 110, 120 during use, the design of the teeth 118, 128 is important. As can be seen in FIG. 12, a surface 118a, 128a of a tooth is contoured with a compound radius wherein the surface is formed by two or more radii. Alternately a series of chamfers or other cuts may be used to achieve the same result. When at least one of the upper cuff 110 and lower cuff 120 is caused to move about its pivot axis, the engagement between teeth 118, 128 will change, i.e., as the upper and lower cuffs 110, 120 are caused to pivot (or at least one is caused to pivot) so too are the teeth 118, 128. Contoured surfaces 118a, 128a enable the teeth 118, 128 to continue to move freely as the pivoted upper cuff 110 and/or lower cuff 120 are caused to rotate. Without the contoured surface 118a, 128a, the teeth 118, 128 would bind when one of the upper cuff 110 and lower cuff 120 pivots, thereby preventing rotation and rendering the knee brace inoperable. The present invention advantageously avoids such a situation with the contoured surface 118a, 128a of the teeth 118, 128. A hinge spring 180 biases free ends 136, 138 of the second parts 114, 124 to maintain alignment of the teeth 118, 128, ensuring smooth rotational movement between the upper cuff 110 and lower cuff 120.

Figure 14:
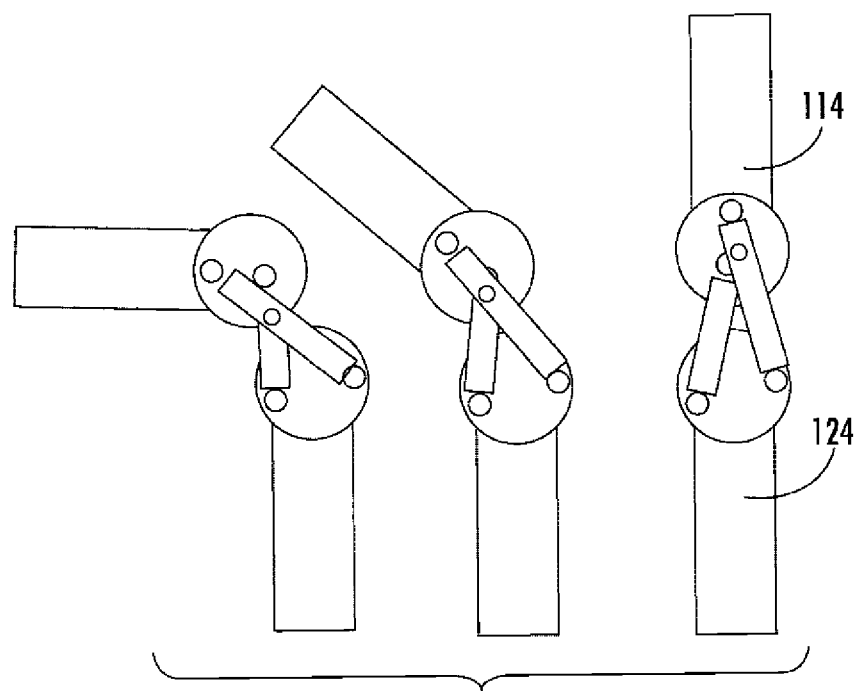
FIG. 14 depicts a four-bar linkage useable as part of an articulation assembly in accordance with an embodiment of the present invention.

It will also be obvious to one skilled in the art that the intent of the invention disclosed herein can be applied to other types of articulation assemblies, for example a four-bar linkage, as depicted in FIG. 14. In such a four-bar linkage, the base 210 and mounts 220 together would form one of the bars, each of the free ends 114, 124 would form a bar, and a fourth bar would be formed from a separate, hinged component.

Referring next to FIGS. 4A, 4B, 5, 6A and 6B, the articulation assembly 200 will now be described in detail. The articulation assembly 200 comprises a base 210, a mount 220 (one for each upper and lower cuff 110, 120) and an adjuster 230. The base 210 has a first side that faces the wearer's knee when the knee brace 100 is in position on the wearer's leg. A surface 214 of the first side is configured to receive a condyle pad 202. The base 210 has a second side with a surface 212 that faces away from the wearer's knee when the knee brace 100 is in position. A base boss 226 extends from the surface 212 and is sized and shaped to receive a pivot pin 222 for each of the upper cuff 110 and lower cuff 120. The pivot pin 222 defines a pivot axis 154 for each of the upper cuff 110 and lower cuff 120 and connects each of them to the base 210 via the mount 220.

Figure 11:
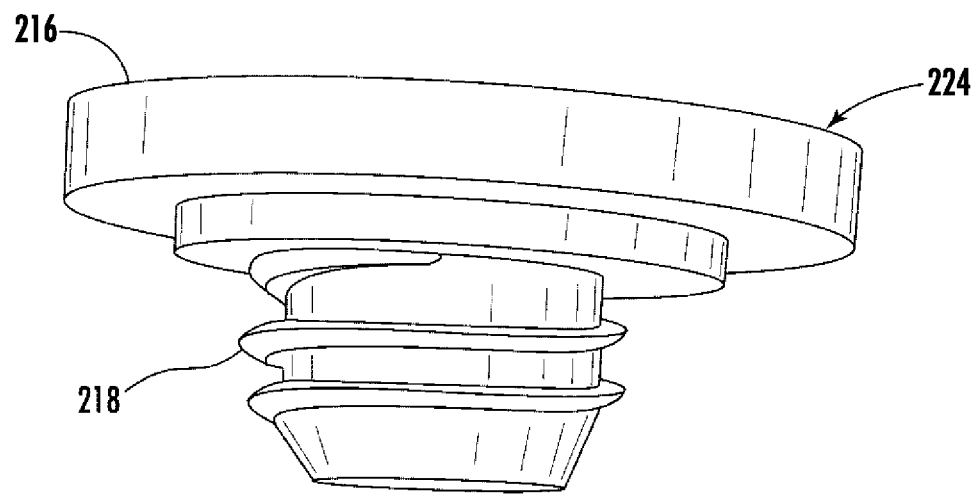
FIG. 11 depicts a rotation pin in accordance with embodiments of the present invention.
Figure 13:
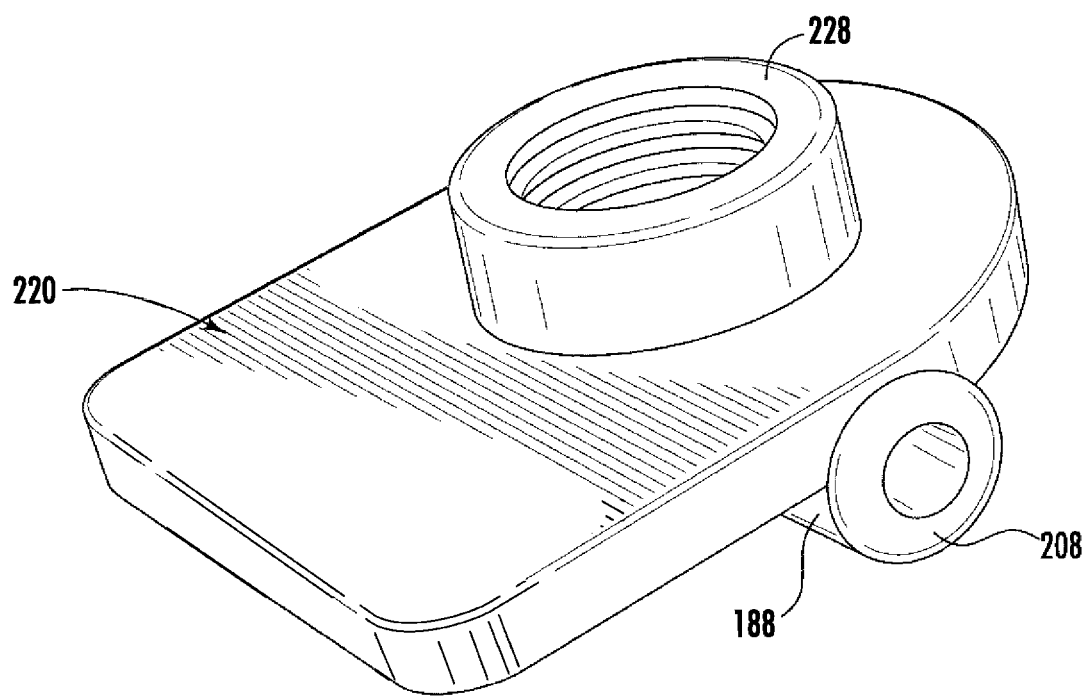
FIG. 13 depicts a detail view of a mount in accordance with an embodiment of the present invention.

As shown in FIG. 13, the mount 220 has a tab 208 having a generally arcuate periphery 188 to facilitate pivoting of the upper cuff 110 and lower cuff 120 about their respective pivot axis 154. The arcuate periphery 188 of the tab 208 of each mount 220 is positioned on or near the surface 212 of the base 210 when the mount 220 is connected to the base 210 by the pivot pin 222. Each mount 220 also has a boss 228 to receive a rotation pin 224 (see, e.g., FIG. 11) to connect each of the upper cuff 110 and lower cuff 120 to its respective mount 220 for rotation about the rotation axis 164. The boss 228 is preferably internally threaded to receive an externally threaded rotation pin 224 that defines a rotation axis 164 for each of the upper cuff 110 and lower cuff 120. The rotation pin 224 may comprise a head section 216 and a stud section 218 having at least an external threaded part complementarily sized and shaped to be received by the internally threaded boss 228. Alternatively, the stud section 218 may be internally threaded and sized and shaped to receive an at least partially externally threaded stud of the of the mount 220 (in place of the boss 228).

Figure 6A:
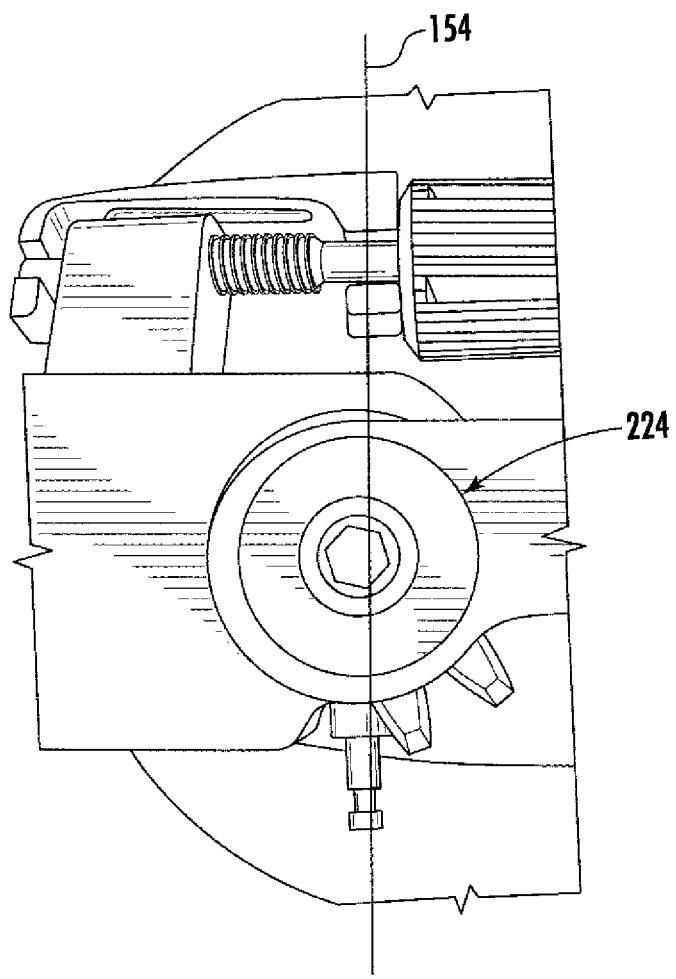
FIGS. 6A and 6B respectively depict a pivot axis and a rotation axis of a knee brace in accordance with an embodiment of the present invention.
Figure 6B:
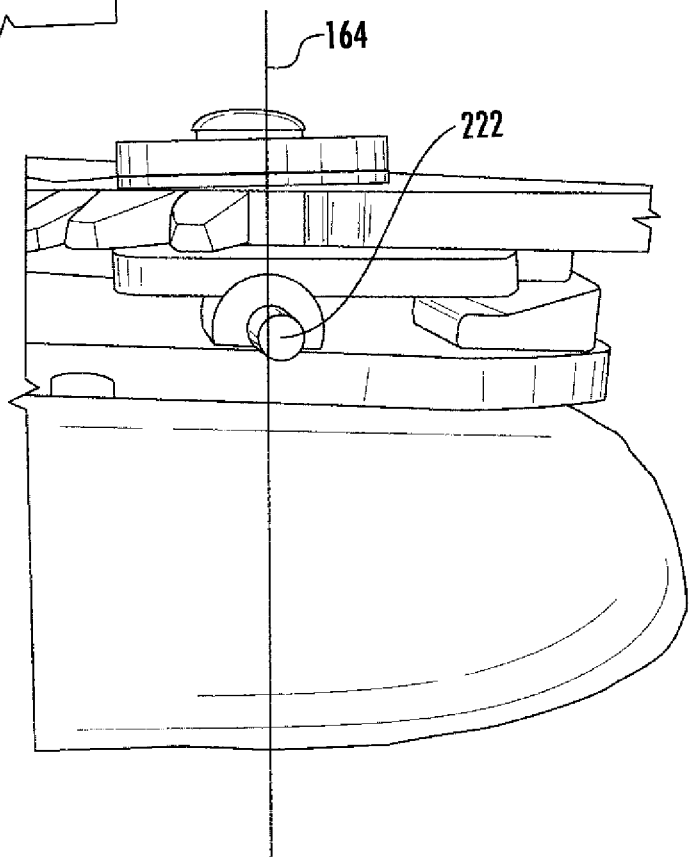

Depicted in FIGS. 6A and 6B is the intersecting relationship between the pivot axes and rotation axes, in accordance with an embodiment of the present invention. Although only the pivot and rotation axes 154, 164 of the lower cuff 120 are shown in FIGS. 6A and 6B, the following description applies as well to the pivot and rotation axes 154, 164 of the upper cuff 110. As discussed herein, the pivot axis 154 of each of the upper cuff 110 and lower cuff 120 is defined by the pivot pin 222 connecting each upper and lower cuff 110, 120 to the articulation assembly 200 via a respective mount 220. The rotation axis 164 of each of the upper cuff 110 and lower cuff 120 is defined by the rotation pin 224 connecting each upper and lower cuff 110, 120 to the articulation assembly 200 via a respective mount 220. Preferably, the pivot axis and rotation axis of the upper cuff 110 intersect, and the pivot axis and rotation axis of the lower cuff 120 intersect, as depicted in FIGS. 6A and 6B. Alternatively, the rotation axis 164 of at least one of the upper cuff 110 and lower cuff 120 may be offset from intersecting its corresponding pivot axis 154. In a preferred embodiment, the axes are offset from intersecting each other so that the pivot axis 154 is located at a location between the rotation axes 164, preferably not between and equidistant from them.

In accordance with embodiments of the present invention, the size of the knee brace when in place on the wearer's extremity defines an envelope about the joint, referred to herein as the brace envelope, is minimized because of the advantageous relational location of the rotation axes and pivot axes. Specifically, the intersecting relation between the axes, or the offset from intersecting relation and location of the pivot axis at a location that is not between and equidistant from the first and second rotation axes.

The articulation assembly 200 also comprises an adjuster 230 for adjusting the angular relationship of certain parts of the knee brace 100, and correspondingly adjusting the effect the knee brace 100 has on the biomechanics of the wearer's knee. In accordance with embodiments of the present invention, and as depicted at least in FIGS. 4A, 4B, 5 and 9, the adjuster 230 comprises a head 236, studs 234a, 234b, and a wedge 240. Although the wedge 240 is depicted in the figures as being generally wedge-shape, it will be obvious to a person skilled in the art and from the disclosure provided herein that the wedge 240 of the present invention is not limited to such a shape. Rather, the wedge 240 of the present invention may comprise a structure of any shape suitable for causing pivotable movement of the upper cuff 110 and lower cuff 120 about the pivot axis 154. Similarly, the head 236 depicted in the figures as being generally tubular is not limited to such a shape, it being obvious to a person skilled in the art and from the disclosure provided herein that other shapes are contemplated by, and within the scope and spirit of the present invention. The adjuster 230 provides a mechanical advantage to the wearer resulting in simple and easy adjustment of the knee brace 100. The adjuster 230 enables adjustments to be made by hand or with ordinary objects such as a coin, i.e., without the need for special tools. The head 236 preferably has a textured surface such as a knurled outer surface comprising a plurality of generally longitudinal grooves 246. The head 236 also preferably comprises a plurality of slots 248 that are sized and shaped to receive an adjustment tool such as, by way of non-limiting example, a coin or other similarly sized and shaped object. It will be obvious to a person skilled in the art that various other types and patterns may be used to create a knurled surface of the head 236 of the present invention. A threaded stud 234a, 234b extends from each end of the head 236, each stud 234a, 234b being rotatable with rotation of the head 236. Threaded studs 234a, 234b are threaded in opposite directions and each engage a threaded through-hole in the wedge 240 such that rotation of the head 236 causes corresponding rotation of each 234a, 234b stud, and simultaneous movement of each wedge 240 towards and away from the head 236. The wedge 240 defines a stop surface 242 to impede rotational movement of the upper cuff 110 and lower cuff 120 (as described in more detail below), and to prevent hyperextension of the knee. Alternately the free end of the upper and lower cuffs may each include an extending surface that contact upon full extension of the leg/knee and prevent hyperextension of the knee.

Figure 5:
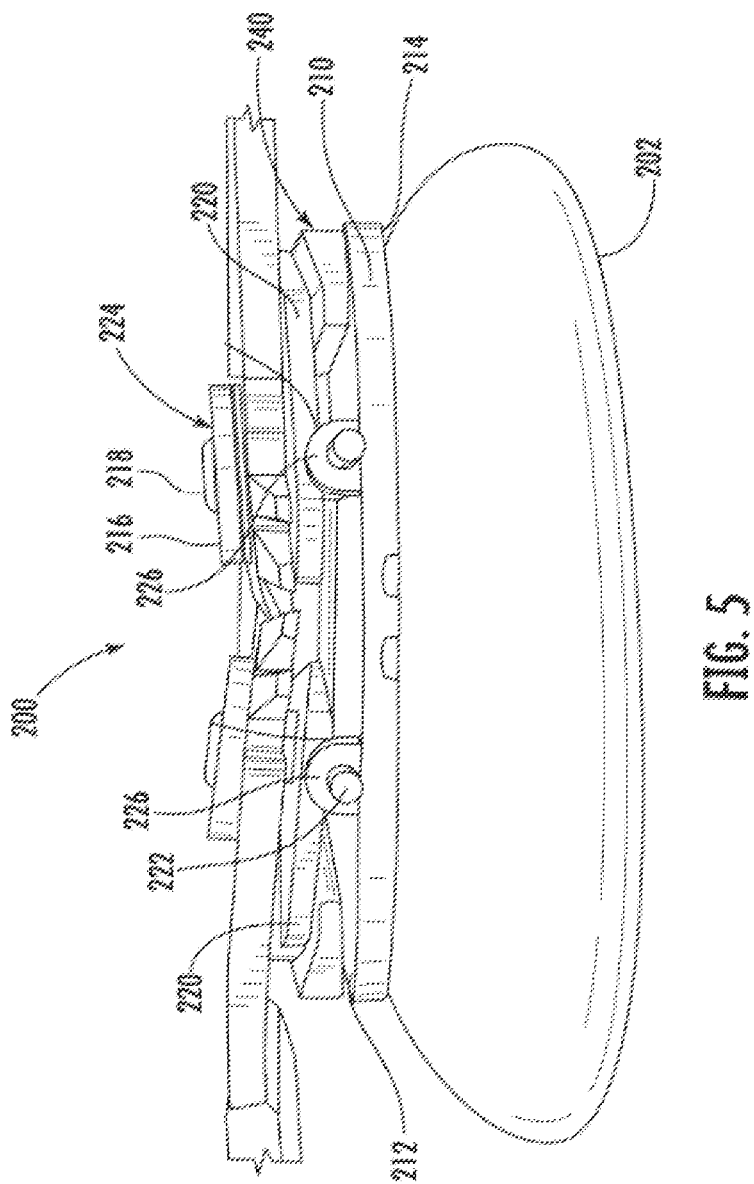
FIG. 5 depicts a side view of an articulation assembly of a knee brace in accordance with an embodiment of the present invention.
Figure 7:
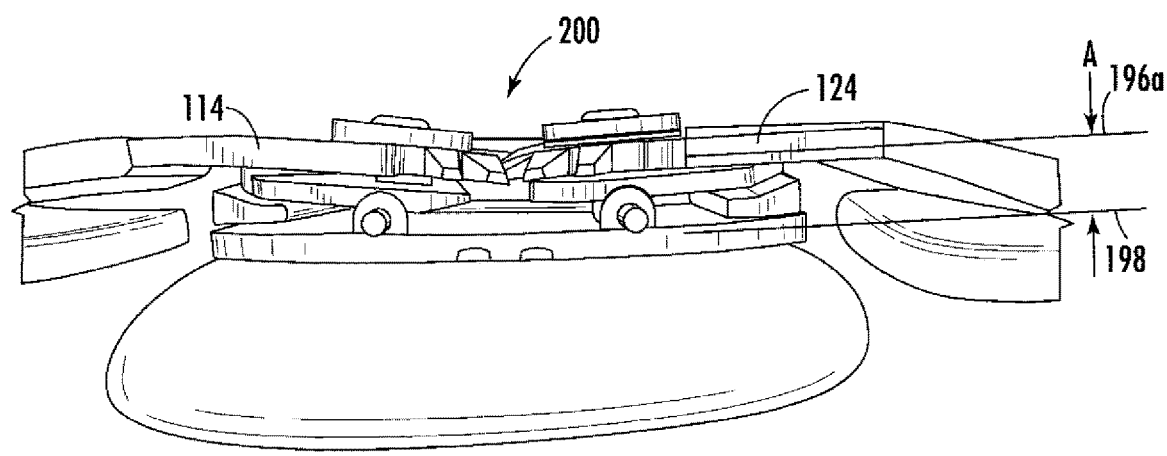
FIG. 7 depicts a side view of an articulation assembly of a knee brace in accordance with an embodiment of the present invention showing a first angular relationship between parts of the knee brace.
Figure 8:
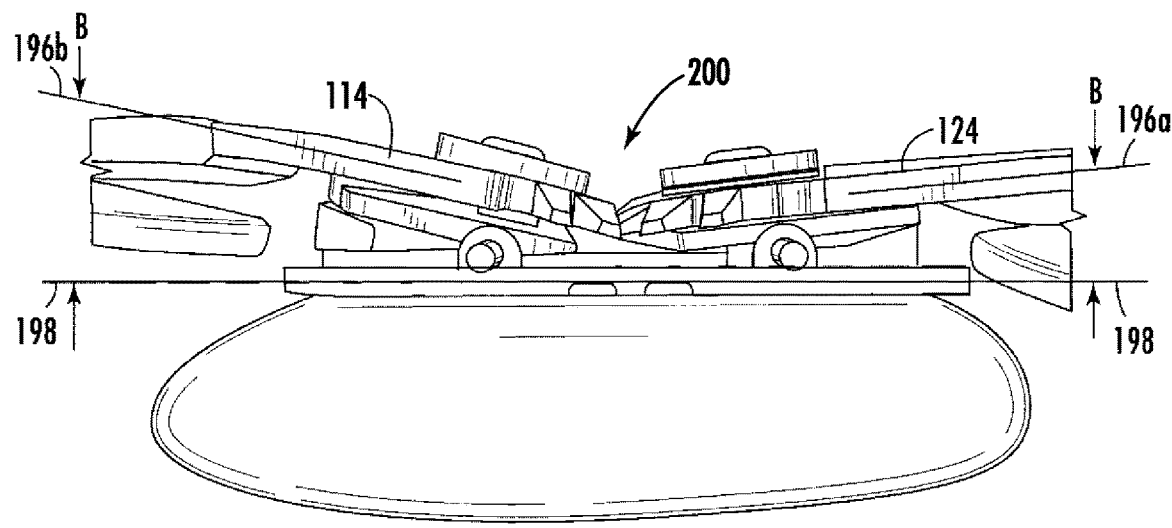
FIG. 8 depicts a side view of an articulation assembly of a knee brace in accordance with an embodiment of the present invention showing a second angular relationship between parts of the knee brace.
Figure 9:
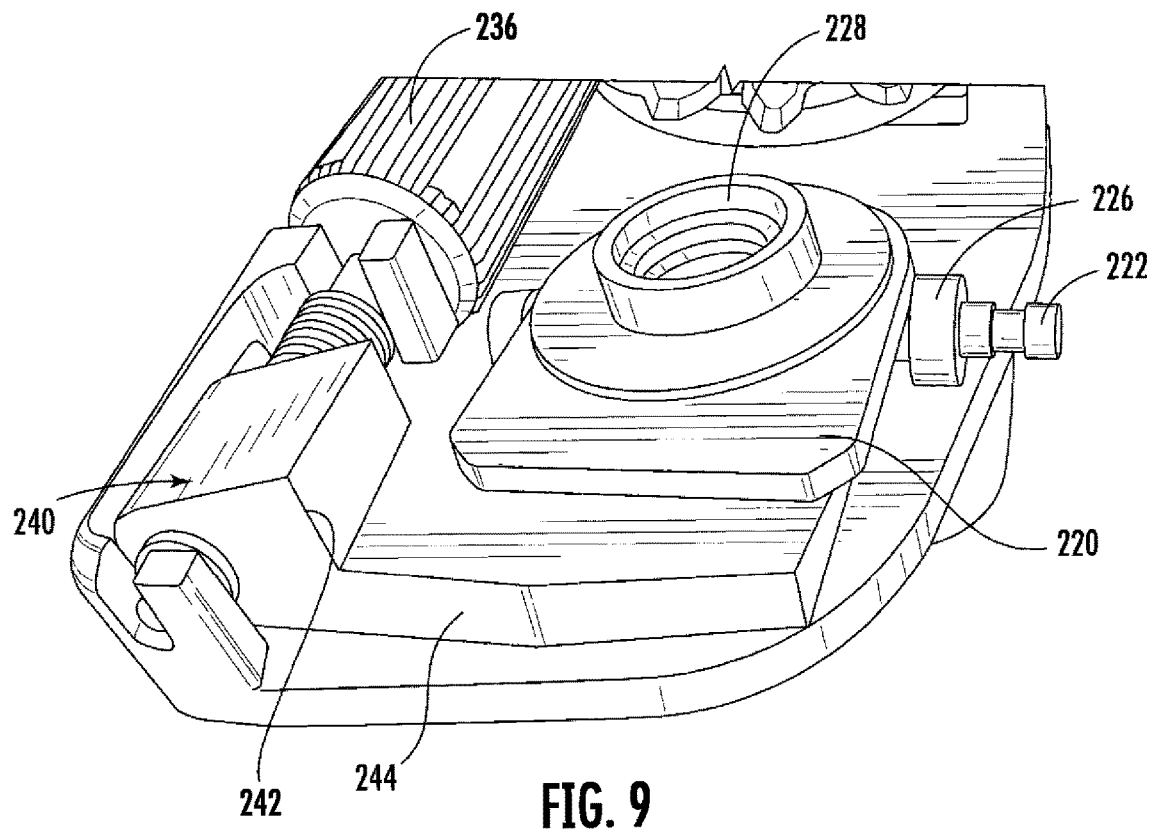
FIG. 9 depicts a perspective side view of parts of an articulation assembly of a knee brace in accordance with an embodiment of the present invention.
Figure 10:
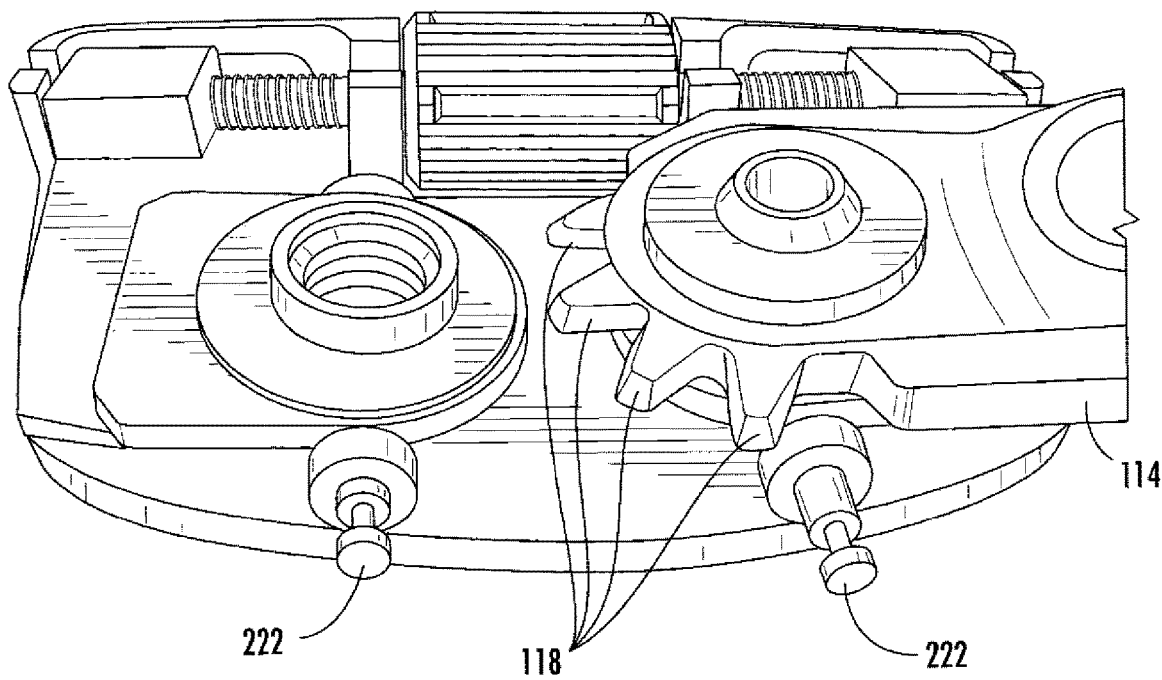
FIG. 10 depicts a perspective view of an articulation assembly of a knee brace in accordance with an embodiment of the present invention.

The wedge 240 also further comprises a ramp 244 that will cause pivotable movement of the upper cuff 110 and lower cuff 120 about the pivot axis 154 based upon the position of the ramp 244. In accordance with a preferred embodiment of the present invention, a user may adjust the knee brace by rotating the head 236 of the adjuster 230, causing rotation of each of the threaded studs 234a, 234b and causing movement of the wedge 240 towards and away from the head 236, which results in movement of the ramp 244. As can be seen in FIGS. 5, 7, and 8, the ramp 244 is positioned to move along (any of contacting, non-contacting, or intermittently contacting) surface 212 towards and away from the pivot pin 222. As the ramp 244 is caused to move towards the pivot pin 222, it will engage the mount 220, causing it to pivot about the pivot axis 154. This will cause a corresponding pivot of each of the upper cuff 110 and lower cuff 120 about its respective pivot axis 154. As the upper cuff 110 and lower cuff 120 are generally fixed in place about the wearer's thigh and calf, such movement of the ramp 244 and the corresponding pivot about the pivot axis 154 will result in a change in the angular relationship between the cuffs 110, 120 and the base 210, also resulting in a change of pressure on the knee joint by the condyle pad 202.

In an alternative embodiment, separate heads 236a, 236b may be provided for the upper cuff 110 and lower cuff 120 respectively. Each head 236a, 236b has a threaded stud 234a, 234b that threadedly engages a threaded through hold in a wedge 240. In this embodiment, the pivot angle of the upper cuff 110 and lower cuff 120 can be separately adjusted using the separate heads 236a, 236b.

In a preferred embodiment, each of the upper cuff 110 and lower cuff 120 can be caused to pivot about its respective pivot axis 154 by a predetermined amount. As can be seen in FIGS. 7 and 8, the second part 114, 124 of each of the upper cuff 110 and lower cuff 120 respectively each define a plane 196a, 196b, and the base 210 defines a plane 198. An angular relationship is defined between the planes 196a, 196b, and 198 based upon the pivot of the upper cuff 110 and lower cuff 120 about the pivot axis 154, which in turn is based upon the position of the ramp 244. Because the rotation axis 164 is angularly fixed with respect to the second part 114, 124, a fixed angular relationship exists between the rotation axes 164 and planes 196a, 196b. However, an angular relationship is also defined between the rotation axis 164 and plane 198, and in a preferred embodiment, this angular relationship is variable. Using the adjuster 230, a wearer can modify the biomechanics of his/her knee by changing the angular relationship between planes 196a, 196b, and 198. A first angular relationship is depicted in FIG. 7 and designated as "A." In this configuration, the condyle pad 202 will rest against the wearer's knee, applying a minimal amount of lateral pressure to the knee and minimally modifying the biomechanics of the knee. With the adjuster 230, the wearer may further modify the biomechanics of his/her knee by causing the ramp 244 to move towards the pivot axis 154, causing each of the upper cuff 110 and lower cuff 120 to pivot about their respective pivot axis 154, and changing the angular relationship between planes 196a, 196b, and 198, designated as "B" in FIG. 8. In this configuration, the condyle pad 202 will exert greater lateral pressure to the wearer's knee, resulting in a greater modification of the biomechanics of that knee. The adjuster 230 thus enables the wearer to set the knee brace 100 for the desired support and comfort.

Because of the construction of the upper cuff 110 and lower cuff 120, and the interconnection of the various parts of the knee brace 100 of the present invention, the amount of pressure imparted by the condyle pad 202 on the wearer's knee is related to a number of factors. A first one is the design and configuration of the upper and lower cuffs 110, 120. Together with the upper and lower sleeves 132, 134, each is designed to snugly fit around a wearer's thigh and calf, and to remaining generally fixed in place while being worn. The interconnection between the second part 114, 124 of each of the upper and lower cuffs 110, 120 and the articulation assembly 200 also impacts the amount of pressure applied by the condyle pad 202 to the knee. As discussed herein, a wearer can change the relationship of these parts and their respective interconnections using the adjuster 230 to modify the angular relationship between the parts and impart more or less pressure to the knee joint. With the upper and lower cuffs 110, 120 essentially being fixed in place on the wearer's thigh and calf, the adjuster 230 is used to modify the amount of pressure imparted by the condyle pad 202 on the wearer's knee.

The complexity of the knee joint and its associated biomechanics are somewhat simplified for discussion of the knee brace of the present invention. Similarly, the discussion of the inventive knee brace 100 may be generalized at times for illustration purposes only. For example, discussion regarding pivotable movement about the pivot axis has been in the context of movement of the upper and lower cuffs 110, 120, respectively about pivot axis 154. Such description may seem to require that the base 210 remain fixed in place to allow the cuff to pivot about the pivot axis. However, it will be obvious to a person skilled in the art, in view of the disclosure provided herein, that neither the base 210 nor the upper and lower cuffs 110, 120 are rigidly fixed in place, and the movement about the pivot axis 154 involves movement of both the upper and lower cuffs 110, 120, and the base 210 relative to each other. Thus, discussion herein regarding pivotable movement about the pivot axis 154 is not dependent upon, nor limited to movement of any one moveable structural component to any one fixed structure component.

Use of the present invention will now be discussed in greater detail, with continued reference to the drawings. The dimensions of the various parts of the knee brace 100 of the present invention may be varied based upon the height, weight, age, etc. of the wearer. The knee brace 100 may also be custom fitted to a specific wearer such that the contour of each of the upper and lower cuff 110, 120 is custom sized and shaped, or the inventive knee brace may be provided in standard, predetermined configurations, or as a one-size-fits-all. The upper and lower sleeves 132, 134 are secured, respectively, to the upper and lower cuffs 110, 120 in any manner that prevents the sleeves 132, 134 from being displaced from their respective cuffs 110, 120. The sleeves 132, 134 each include straps, connectors, clips, clasps, etc. necessary to secure the sleeve 132, 134 and corresponding cuff 110, 120 in place. Once the knee brace 100 is firmly in place on the wearer's leg, the brace 100 should not significantly slide up or down when in use. The knee brace 100 is positioned on the wearer's leg so that the condyle pad 202 is located proximate with, and preferably in contact with a medial or lateral side of the wearer's knee. The adjuster 230 is initially set so that the angle between planes 196a, 196b, and 198 is minimal, as is the amount of lateral pressure imparted on the knee joint by the condyle pad 202. The adjuster 230 with one head 236 or separate heads 236a, 236b is then used by the wearer or another to adjust the amount of pressure from the condyle pad 202 by causing pivotable movement of the upper and lower cuffs 110, 120 about the pivot axis 154, resulting in imposition of greater or lesser force by the condyle pad 202 on the knee joint and modification of the biomechanics of the knee. Such modification can result in compartmental weight-bearing shift and relief of compartmental pressure, discomfort and pain.

Various parts and surfaces of the knee brace 100 of the present invention contact each other. Such surfaces may be treated, coated, or otherwise modified to facilitate smooth, repetitive movement. Materials used to treat, coat, or otherwise modify the various parts and surfaces may include, by way of non-limiting example, Teflon®, lubricants sold by Dicronite®, and other now know, or hereafter developed lubricating materials.

It will be obvious to a person of ordinary skill in the art, from the detailed disclosure provided herein, that the present invention is not limited to the embodiments disclosed herein. The inventor has discovered an improved knee brace by locating a pivot axis and rotation axis of a single cuff and articulation assembly to intersect with each other, or to be offset from intersecting such that the pivot axis is still located in a preferred location to yield the improvements of the present invention, which include, but are not limited to, improved biomechanical performance and a smaller knee brace. In a knee brace with upper and lower cuffs, the pivot axis for each of the upper and lower cuffs is offset from intersecting its corresponding rotation axis such that neither pivot axis is located at a location that is between and equidistant from its respective rotation axis. The present invention is thus not limited in spirit nor scope to the embodiments disclosed and claimed herein, but rather extends to all now known and hereafter developed embodiments that comprise the inventive aspects disclosed herein.

Modifications to embodiments of the present invention are possible without departing from the scope of the invention as defined by the accompanying claims. Expressions such as "including," "comprising," "incorporating," "consisting of," "have," "is," used to describe and claim the present invention are intended to be construed in a non-exclusive manner, namely allowing for articles, components or elements not explicitly described herein also to be present. Reference to the singular is to be construed to relate to the plural, where applicable.

Although specific example embodiments have been described, it will be evident that various modifications and changes may be made to these embodiments without departing from the broader scope of the inventive subject matter described herein. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This description, therefore, is not to be taken in a limiting sense, and the scope of various embodiments is defined only by the appended claims, along with the full range of equivalents to which such claims are entitled.

What is claimed is:

1. A brace wearable on an extremity of a wearer, the extremity having a joint, the brace comprising:
   a first cuff placeable on the extremity;
   an articulation assembly connected with the first cuff, wherein the first cuff is movable with respect to the articulation assembly about a first location defining a first pivot axis between the first cuff and articulation assembly, and wherein the first cuff is movable with respect to the articulation assembly about a second location defining a first rotation axis between the first cuff and articulation assembly, wherein the first pivot axis and the first rotation axis intersect each other;
   wherein the articulation assembly further comprises:
   a base;
   a mount connected to the base at the first location, and connected to the first cuff at the second location; and
   an adjuster manipulable to cause the first cuff to pivot about the first pivot axis; and
   wherein the first cuff further comprises a second part defining a first plane, and wherein the base defines a second plane, and wherein the first rotation axis intersects the first plane at a fixed angle, and the second plane at a variable angle.

2. A brace according to claim 1, further comprising a second cuff placeable on the extremity, the articulation assembly being connected with the second cuff, wherein the second cuff is movable with respect to the articulation assembly about a third location defining a second pivot axis between the second cuff and the articulation assembly, and wherein the second cuff is movable with respect to the articulation assembly about a fourth location defining a second rotation axis between the second cuff and the articulation assembly, wherein the second pivot axis and the second rotation axis intersect each other;

wherein the articulation assembly further comprises:

a base;

a first mount connected to the base at the first location, and connected to the first cuff at the second location;

a second mount connected to the base at the third location, and connected to the second cuff at the fourth location; and an adjuster manipulable to cause the first cuff to pivot about the first pivot axis and the second cuff to pivot about the second pivot axis.

3. A brace according to claim 2, wherein the first cuff is rotatable about the first rotation axis, and the second cuff is rotatable about the second rotation axis, wherein the knee brace further comprises a gear having a first part defined on the first cuff, and a second part defined on the second cuff, wherein the first part and the second part engage each other such that movement of one of the first cuff and second cuff causes movement of the other one of the first cuff and second cuff.

4. A brace according to claim 3, wherein the gear further comprises first teeth on the first cuff, and second teeth on the second cuff, wherein the first teeth and the second teeth movably interlockingly engage such that rotational movement of one of the first cuff and second cuff causes corresponding rotational movement of the other one of the first cuff and second cuff.

5. A brace according to claim 4, wherein a surface on at least one of the first and second teeth is contoured.

6. A brace according to claim 2, wherein the adjuster further comprises one of a head manipulable to cause the first cuff to pivot about the first pivot axis and the second cuff to pivot about the second pivot axis, or a first head and a second head, the first head being manipulable to cause the first cuff to pivot about the first pivot axis, and the second head manipulable to cause the second cuff to pivot about the second pivot axis.

7. A brace according to claim 2, wherein the second cuff is movable with respect to the articulation assembly in a second pivot direction about the third location defining the second pivot axis between the second cuff and the articulation assembly, and wherein the second cuff is movable with respect to the articulation assembly in a second rotation direction about the fourth location defining the second rotation axis between the second cuff and the articulation assembly.

8. A brace according to claim 1, wherein the adjuster comprises:

a wedge movable along a surface of the mount to cause the first cuff to pivot about the first pivot axis;

a stud engaged with a part of the wedge such that manipulation of the stud causes movement of the wedge along the surface of the mount; and a head manipulable to cause manipulation of the stud.

9. A brace according to claim 1, wherein the variable angle is variable by the adjuster.

10. A brace according to claim 1, wherein the mount further comprises a boss, and wherein the articulation assembly further comprises a rotation pin connectable with the boss to connect the mount and the first cuff together at the second location.

11. A brace according to claim 1, wherein the mount further comprises a tab, and wherein the articulation assembly further comprises a pivot pin connectable with the tab to connect the mount and the first cuff together at the first location.

12. A brace according to claim 1, wherein the first cuff is movable with respect to the articulation assembly in a first pivot direction about the first location defining the first pivot axis between the first cuff and articulation assembly, and wherein the first cuff is movable with respect to the articulation assembly in a first rotation direction about the second location defining the first rotation axis between the first cuff and articulation assembly.

* * * * *